United States Patent [19]

Uemura et al.

[11] Patent Number: 4,695,467
[45] Date of Patent: Sep. 22, 1987

[54] SUSTAINED RELEASE TABLET

[75] Inventors: Toshinobu Uemura, Kishiwada; Kiyohide Shinooka, Nishinomiya; Tokuaki Kajiho, Kobe, all of Japan

[73] Assignee: Fujisawa Pharmaceutical Co., Ltd., Osaka, Japan

[21] Appl. No.: 751,866

[22] Filed: Jul. 5, 1985

[30] Foreign Application Priority Data

Jul. 12, 1984 [JP] Japan ............................... 59-145495

[51] Int. Cl.$^4$ .......................... A61K 9/22; A61K 9/16
[52] U.S. Cl. .................................... 424/502; 424/464; 424/465; 424/468; 424/469; 424/470; 424/475; 424/476; 424/489; 514/200; 514/356; 514/960
[58] Field of Search .................................... 424/19–22, 424/38

[56] References Cited

U.S. PATENT DOCUMENTS 4,308,251 12/1981 Dunn et al. ........................... 424/17
4,454,108 6/1984 Iida et al. .............................. 424/16

FOREIGN PATENT DOCUMENTS 57-53763 11/1982 Japan.
2053681A 2/1981 United Kingdom.

*Primary Examiner*—Shep K. Rose
*Attorney, Agent, or Firm*—Oblon, Fisher, Spivak, McClelland, & Maier

[57] ABSTRACT

The invention relates to a sustained release tablet which comprises easily disintegrable granules containing
(a) a drug,
(b) a disintegrating agent selected from the group consisting of starch derivatives, gums, cellulose derivatives and ion-exchange resins, and
(c) a water soluble polymer selected from the group consisting of cellulose derivatives, synthetic water soluble polymers and polysaccharides, the surfaces of which granules are treated solely with a wax selected from the group consisting of plant or animal wax, hydrogenated oils and paraffin.

13 Claims, No Drawings

SUSTAINED RELEASE TABLET

The present invention relates to sustained release tablets and a process for preparation thereof. More particularly, it relates to sustained release tablets each comprising easily disintegrable granules each containing drug optionally together with water soluble polymer, and wax, from which tablets, by the control of the disintegration thereof, the drug gets released in a sustained manner and, moreover, at an almost constant rate, so that the effect of the drug is maintained over a long period of time and relates to a process for preparation thereof.

Pharmaceutical preparations, from which a drug is released continuously, so that the effect of the drug can be maintained over a long period of time are useful pharmaceutical preparations which have so far been studied for the purpose of reducing the frequency to be taken by patients or for the purpose of keeping the blood concentration of a drug below a certain level, in case that the toxicity or adverse effects of the drug may increase above said level.

Prior art developed for such purposes includes a pharmaceutical preparation comprising drug-containing granules provided with a coating layer and a pharmaceutical preparation comprising a continuous matrix with a drug dispersed therein (matrix tablet). In these pharmaceutical preparations, the coating layer or matrix comprises a substance insoluble or hardly soluble in aqueous body fluids and the release of the drug is controlled by means of the resistance of said coating layer or matrix against the diffusion of the drug therethrough. These pharmaceutical preparations are characterized in that the granules to be coated or the initial granules to be used in making matrix tablets are as hardly disintegrable as possible.

The release of the drug from such pharmaceutical preparations provided by the prior art is driven by the gradient of the drug concentration resulting from penetration of water (diffusion rate-determining). In this mode of release, at the later stage of release, the rate of the release decreases due to the decrease in the concentration gradient and the increase in the distance of diffusion, and therefore the amount of the release is approximately proportional to the square root of the time.

Enteric-coated preparation is referred to as another type of sustained release preparation. The release of the drug from an enteric-coated preparation get delayed by providing a coating layer soluble only after arrival at the intestine, and the extent of this delay is determined by the rate at which said pharmaceutical preparation is gradually discharged from the stomach into the intestine. By combining such enteric portion with a usual portion soluble in the stomach, the release of the drug can be rendered continuous.

The pharmaceutical preparations of the prior art mentioned above have the following drawbacks:
  (i) Pharmaceutical preparations, wherein the rate of the drug release therefrom is controlled by the diffusion rate-determining mechanism, have a drawback that the rate of the drug release gradually slows down with the lapse of time. When the said technique is applied to a hardly soluble drug, the dissolution is so insufficient that such preparation is not practical.
  (ii) When enteric-coated preparation is utilized, the problem lies in that the release of the drug is controlled by the pH.

The pH value in the digestive tract varies depending on the site. It also varies in point of time within a day and, further, depending on the patient's mental condition. Therefore since the release is influenced by such variations, the desired purpose cannot always be attained. In case of anacidity often found in the aged, since even the enteric-coated portion dissolves already in the stomach, there is a risk that a large amount of drug gets released at the same time. Furthermore, since the release rate of drug is under the control of the rate of discharge of the enteric-coated preparation from the stomach, the amount of food and so on present in the stomach at the time of taking said preparation is an important factor. However, patients do not always take said preparations in accordance with the direction, so that the case that the desired purpose cannot be attained may happen.

Not only in case of enteric-coated preparations, but also in case of pharmaceutical preparations controlled by the diffusion rate-determining mechanism, since the properties of the drug itself (e.g. solubility) vary depending on the pH value of the aqueous medium, the release rate of the drug is influenced by the change of the pH value.

As mentioned above, the pharmaceutical preparations of the prior art have a drawback that the release rate of the drug slows down with the lapse of time and a drawback that said rate depends on the pH value of the part where the pharmaceutical preparation dissolves, and therefore, the difficulty exists in how to control the blood concentration of the drug.

The purpose of the present invention is to solve the problems as stated above and to provide a pharmaceutical preparation, wherein the release rate of the drug is nearly constant (zero order release) and the change of the release rate of the drug by the change of the stirring intensity, the pH value or the like is little, and to provide a process for the preparation thereof.

Incidentally, as one method that gives a resolution to the above problems, a technique has been given (Japanese Publication No. 53763/1982), which comprises coating the instantaneously disintegrable granules containing drug, with the coating layer consisting of wax, water soluble polymer and nonionic surfactant having HLB not more than 9 and after that, compressing the resultant coated granules into tablets to give sustained release tablets.

However, as to the surfactant to be used therein, it is preferable to avoid using the surfactant from the point of view of its irritation against human body, its safety for human body, the stability of the tablets themselves and the like.

Besides, in this method, since there are many factors to control the drug release, one can understand, in case of applying this method to a certain drug, there is difficulty in determining concretely the components and the combination ratio thereof.

As described in detail below, the present invention achieves its purpose by a simple method, which comprises compressing the wax-treated, easily disintegrable granules each containing drug optionally together with water soluble polymer, into tablets and therefore, the present invention overcomes even the defects of the above-mentioned method.

The sustained release tablet of the present invention comprises the easily disintegrable granules, each containing drug, and wax; or comprises the easily disintegrable granules, each containing drug together with water soluble polymer, and wax, and can be prepared, for example, by treating the surfaces of said easily disintegrable granules with wax and after that, compressing them into tablets.

The easily disintegrable granules, each containing drug, can be prepared by converting a mixture of drug, disintegrating agent [e.g. various starch derivatives (e.g. corn starch, potato starch, rice starch, α-starch, carboxymethyl starch, etc.), gums (e.g. gum arabic), cellulose derivatives (e.g. calcium carboxymethylcellulose, sodium carboxymethylcellulose, low substituted hydroxypropylcellulose, cross-linked sodium carboxymethylcellulose, etc.), various ion-exchange resins (e.g. potassium polymethacrylate, etc.], excipient (e.g. lactose, sucrose, mannitol, etc.) and commonly used additives in this field of the art, into granules according to a conventional manner.

The amount of the disintegrating agent is preferably 10 to 60 weight percent of the whole granule components, but the amount of the disintegrating agent is not restricted to said range and may be determined fittingly depending on the property of the drug to be used, the intended duration of the drug release or the like and some kinds of disintegrating agents may be used as a mixture thereof.

The easily disintegrable granules, each containing drug together with water soluble polymer, can be prepared by converting a mixture of drug, water soluble polymer [e.g. cellulose derivatives (e.g. hydroxypropylmethylcellulose, methylcellulose, hydroxypropylcellulose, carboxymethylcellulose, etc.), synthetic water soluble polymers (e.g. polyvinylpyrrolidone, cross-linked polyvinylpyrrolidone, polyethylene oxide, etc.), polysaccharides (e.g. pullulan, dextran, etc.), etc.], disintegrating agent and excipient, both as mentioned above, and additives commonly used in this field of the art, into granules according to a conventional manner.

In this case, the preferable amount of disintegrating agent to be used may be also the same as stated in the former case.

And the amount of water soluble polymer is preferably 2.5 to 45 weight percent (more preferably 5 to 30 weight percent of the whole granule components, but the amount of water soluble polymer is not restricted to said range and may be determined fittingly depending on the property of the drug to be used, the intended duration of the drug release or the like and some kinds of water soluble polymers may be used as a mixture thereof.

As stated above, in the present invention, the distinct feature consists in making the granules, each containing drug optionally together with water soluble polymer, easily disintegrable.

In these procedures, in case that the drug to be used is hardly soluble and so when the drug itself is used, the absorption thereof into blood seems to be insufficient, the granules may be prepared after previously converting said drug into certain easily soluble preparation form such as a solid dispersion composition or the like.

Said solid dispersion composition can be prepared, for example, by uniformly dispersing the drug in water soluble polymer (e.g. hydroxypropylmethylcellulose).

Next, the granules produced in the above manner are subjected to wax treatment.

The wax to be used in this step includes all kinds of wax insoluble or hardly soluble in water, and may include plant or animal wax (e.g. carnauba wax, bees wax, etc.), various hydrogenated oils (e.g. hydrogenated soybean oil, hydrogenated castor oil, etc.) paraffin (e.g. paraffin wax, microcrystalline wax, etc.) and the like. The wax as mentioned above may be used as a mixture thereof.

The wax treatment can be carried out by kneading the above granules with molten wax, followed by drying and sieving. However, the method of wax treatment is not restricted to said procedure.

The amount of the wax to be used is fittingly determined depending on the property of the drug to be used, the intended duration of the drug release or the like; and the preferable amount of the wax is 20 to 65 weight percent, most preferably 30 to 55 weight percent of the whole components of the tablet.

The kind of the wax to be used may be determined fittingly depending on the property of the drug to be used, the amount of the wax to be used, the intended duration of the drug release or the like.

After treating the surfaces of the granules with wax as stated above, a lubricant such as magnesium stearate or the like is dispensed and the resultant mixture is compressed into tablets by a conventional manner and thereby the sustained release tablets of the present invention can be prepared.

The present invention is explained according to the examples in the following.

The chemical names and structural formulas of the drugs used in the examples are as follows :
(1) Designation used in the examples :
Dihydropyridine A compound (vasodilator) Chemical name :
Isopropyl 6-cyano-5-methoxycarbonyl-2-methyl-4-(3-nitrophenyl)-1,4-dihydropyridine-3-carboxylate
Structural formula :

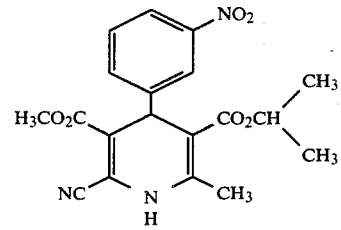

(2) Designation used in the examples :
Cephalosporin A compound (antibiotics)
Chemical name : 7-[2-(2-Aminothiazol-4-yl)-2-carboxymethoxyiminoacetamido]-3-vinyl-3-cephem-4-carboxylic acid (synisomer)
Structural formula:

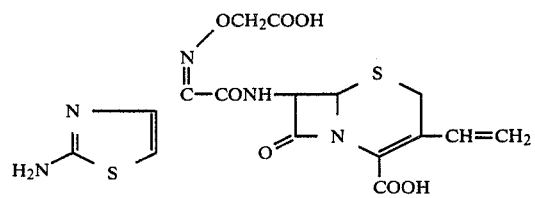

(3) Designation used in the examples:

Chloropyridine compound (an agent for the treatment of vascular disorder)
Chemical name:
A clathrate compound of 2-nitroxymethyl-6-chloropyridine with β-cyclodextrin (mole ratio 1:1)
Structural formula: 2-Nitroxymethyl-6-chloropyridine is a compound having the following structural formula:

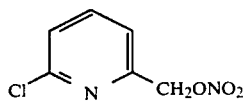

EXAMPLE 1

Dihydropyridine A compound (20 g) and hydroxypropylmethylcellulose (60 g) were dissolved in a 1:1 mixture of ethanol and methylene chloride. A homogeneous mixture of low substituted hydroxypropylcellulose (90 g) and lactose (30 g) was added to the above solution and the resultant mixture was kneaded. The resultant mixture was then dried at 60° C. for 4 hours, ground in a mill and sieved to give granules passing through a 32-mesh sieve. (At this stage, dihydropyridine A compound itself was converted into granules of solid dispersion composition containing dihydropyridine A compound.)

The granules prepared in the above step (110 g) and molten hydrogenated soybean oil (110 g) were cooled to the room temperature with kneading and then the mixture was sieved to give granules passing through a 20-mesh sieve (wax-treated granules.)

The above wax-treated granules (200 g) were mixed with magnesium stearate (0.4 g) and the resultant mixture was compressed into tablets to give sustained release tablets.

These tablets each had an outside diameter of 7 mm and the following composition:

| | |
|---|---|
| Dihydropyridine A compound | 8.0 mg |
| Hydroxypropylmethylcellulose (c.v. 6 cps)* | 24.0 mg |
| Low substituted hydroxypropylcellulose | 36.0 mg |
| Lactose | 12.0 mg |
| Hydrogenated soybean oil | 80.0 mg |
| Magnesium stearate | 0.3 mg |
| | 160.3 mg |

*c.v.: coefficient of viscosity
cps: centi poise
(hereinafter the same abbreviations are used)
(The viscosity is closely related to the molecular weight and the higher the viscosity is, the higher the molecular weight is.)

EXAMPLE 2

Tablets each having the composition given below were produced according to a similar manner to that of Example 1.

| | |
|---|---|
| Dihydropyridine A compound | 8.0 mg |
| Hydroxypropylmethylcellulose (c.v. 6 cps) | 24.0 mg |
| Low substituted hydroxypropylcellulose | 24.0 mg |
| Lactose | 24.0 mg |
| Hydrogenated soybean oil | 80.0 mg |
| Magnesium stearate | 0.3 mg |
| | 160.3 mg |

EXAMPLE 3

Tablets each having the composition given below were produced according to a similar manner to that of Example 1.

| | | |
|---|---|---|
| (1) | Dihydropyridine A compound | 8.0 mg |
| | Hydroxypropylmethylcellulose (c.v. 6 cps) | 24.0 mg |
| | Low substituted hydroxypropylcellulose | 19.2 mg |
| | Lactose | 28.8 mg |
| | Hydrogenated soybean oil | 53.3 mg |
| | Magnesium stearate | 0.3 mg |
| | | 133.6 mg |
| (2) | Dihydropyridine A compound | 8.0 mg |
| | Hydroxypropylmethylcellulose (c.v. 6 cps) | 24.0 mg |
| | Low substituted hydroxypropylcellulose | 36.0 mg |
| | Lactose | 12.0 mg |
| | Carnauba wax | 40.0 mg |
| | Paraffin wax | 40.0 mg |
| | Magnesium stearate | 0.3 mg |
| | | 160.3 mg |

EXAMPLE 4

Cephalosporin A compound (purity, 89.4%; 20 g) and low substituted hydroxypropylcellulose (6.7 g) were mixed homogeneously and was added thereto 10.8 ml of 5% (weight/volume) aqueous solution of hydroxypropylmethylcellulose (c.v. 6 cps). The resultant mixture was kneaded, then dried at 50° C. for 4 hours, and sieved to give granules passing through a 32-mesh sieve.

A mixture of the granules prepared in the above step (24 g) and molten carnauba wax (16 g) was cooled to the room temperature with kneading. The resultant mixture was then sieved to give granules passing through a 20-mesh sieve (wax-treated granules).

The above wax-treated granules were compressed into tablets according to a conventional manner to give sustained release tablets, each having the following composition.

| | |
|---|---|
| Cephalosporin A compound (purity, 89.4%) | 139.8 mg |
| | (125 mg potency) |
| Hydroxypropylmethylcellulose (c.v. 6 cps) | 3.8 mg |
| Low substituted hydroxypropylcellulose | 46.6 mg |
| Carnauba wax | 126.8 mg |
| Magnesium stearate | 0.6 mg |
| | 317.6 mg |

EXAMPLE 5

Tablets each having the composition given below were prepared according to a similar manner to that of Example 4.

| | |
|---|---|
| Cephalosporin A compound (purity, 89.4%) | 94.3 mg |
| | (84.3 mg potency) |
| Hydroxypropylmethylcellulose (c.v. 6 cps) | 6.7 mg |
| Low substituted hydroxypropylcellulose | 67.4 mg |
| Hydrogenated castor oil | 101.1 mg |
| Hydrogenated soybean oil | 67.4 mg |
| Magnesium stearate | 0.7 mg |
| | 337.6 mg |

EXAMPLE 6

Tablets each having the composition given below were prepared according to a similar manner to that of Example 4.

| (1) | Chloropyridine compound | 58.4 mg |
|---|---|---|
| | Hydroxypropylmethylcellulose (c.v. 6 cps) | 16.2 mg |
| | Low substituted hydroxypropylcellulose | 87.6 mg |
| | Hydrogenated castor oil | 64.9 mg |
| | Hydrogenated soybean oil | 43.3 mg |
| | Magnesium stearate | 0.5 mg |
| | | 270.9 mg |
| (2) | Chloropyridine compound | 58.4 mg |
| | Hydroxypropylmethylcellulose (c.v. 6 cps) | 16.2 mg |
| | Low substituted hydroxypropylcellulose | 87.6 mg |
| | Hydrogenated castor oil | 97.3 mg |
| | Hydrogenated soybean oil | 64.9 mg |
| | Magnesium stearate | 0.6 mg |
| | | 325.0 mg |

EXAMPLE 7

Cephalosporin A compound (purity : 89.4%) (14 g), low substituted hydroxypropylcellulose (8.5 g) and hydroxypropylmethylcellulose (c.v. 4000 cps) (2.25 g) were mixed homogeneously and then 2.5% (weight-/volume) aqueous solution of hydroxypropylmethylcellulose (c.v. 4000 cps) (10 ml) as binder was added thereto and the resultant mixture was kneaded. After that, the mixture was dried at 60° C. for 4 hours and sieved to give granules passing through a 32-mesh sieve.

A mixture of the granules prepared in the above step (20 g) and a molten mixture of hydrogenated castor oil (16 g) and hydrogenated soybean oil (4 g) was cooled to the room temperature with kneading and then sieved to give granules passing through a 20-mesh sieve (wax-treated granules).

The above wax-treated granules were compressed into tablets according to a conventional manner to give sustained release tablets, each having the following composition.

| Cephalosporin A compound (purity, 89.4%) | 93.2 mg |
|---|---|
| | (83.3 mg potency) |
| Hydroxypropylmethylcellulose (c.v. 4000 cps) | 16.6 mg |
| Low substituted hydroxypropylcellulose | 56.6 mg |
| Hydrogenated castor oil | 133.2 mg |
| Hydrogenated soybean oil | 33.3 mg |
| Magnesium stearate | 0.7 mg |
| | 333.6 mg |

EXAMPLE 8

Tablets each having the composition given below were prepared according to a similar manner to that of Example 7.

| (1) | Cephalosporin A compound | 93.2 mg |
|---|---|---|
| | (purity, 89.4%) | (83.3 mg potency) |
| | Hydroxypropylmethylcellulose (c.v. 400 cps) | 16.6 mg |
| | Low substituted hydroxypropylcellulose | 56.6 mg |
| | Hydrogenated castor oil | 133.2 mg |
| | Hydrogenated soybean oil | 33.3 mg |
| | Magnesium stearate | 0.7 mg |
| | | 333.6 mg |
| (2) | Cephalosporin A compound | 93.2 mg |
| | (purity, 89.4%) | (83.3 mg potency) |
| | Hydroxypropylmethylcellulose (c.v. 50 cps) | 16.6 mg |
| | Low substituted hydroxypropylcellulose | 56.6 mg |
| | Hydrogenated castor oil | 133.2 mg |
| | Hydrogenated soybean oil | 33.3 mg |
| | Magnesium stearate | 0.7 mg |
| | | 333.6 mg |
| (3) | Cephalosporin A compound | 93.2 mg |
| | (purity, 89.4%) | (83.3 mg potency) |
| | Hydroxypropylmethylcellulose (c.v. 6 cps) | 16.6 mg |
| | Low substituted hydroxypropylcellulose | 56.6 mg |
| | Hydrogenated castor oil | 133.2 mg |
| | Hydrogenated soybean oil | 33.3 mg |
| | Magnesium stearate | 0.7 mg |
| | | 333.6 mg |

EXAMPLE 9

Tablets each having the composition given below are prepared according to a similar manner to that of Example 7.

| (1) | Chloropyridine compound | 58.4 mg |
|---|---|---|
| | Hydroxypropylmethylcellulose (c.v. 4000 cps) | 16.2 mg |
| | Low substituted hydroxypropylcellulose | 87.6 mg |
| | Hydrogenated castor oil | 64.9 mg |
| | Hydrogenated soybean oil | 43.3 mg |
| | Magnesium stearate | 0.5 mg |
| | | 270.9 mg |
| (2) | Chloropyridine compound | 58.4 mg |
| | Hydroxypropylmethylcellulose (c.v. 400 cps) | 16.2 mg |
| | Low substituted hydroxypropylcellulose | 87.6 mg |
| | Hydrogenated castor oil | 64.9 mg |
| | Hydrogenated soybean oil | 43.3 mg |
| | Magnesium stearate | 0.5 mg |
| | | 270.9 mg |
| (3) | Chloropyridine compound | 58.4 mg |
| | Hydroxypropylmethylcellulose (c.v. 50 cps) | 16.2 mg |
| | Low substituted hydroxypropylcellulose | 87.6 mg |
| | Hydrogenated castor oil | 64.9 mg |
| | Hydrogenated soybean oil | 43.3 mg |
| | Magnesium stearate | 0.5 mg |
| | | 270.9 mg |

EXAMPLE 10

Tablets each having the composition given below are prepared according to a similar manner to that of Example 7.

| (1) | Chloropyridine compound | 58.4 mg |
|---|---|---|
| | Polyvinylpyrrolidone (molecular weight: $3.6 \times 10^5$) | 16.2 mg |
| | Low substituted hydroxypropylcellulose | 87.6 mg |
| | Carnauba wax | 54.1 mg |
| | Paraffin wax | 54.1 mg |
| | Magnesium stearate | 0.5 mg |
| | | 270.9 mg |
| (2) | Chloropyridine compound | 58.4 mg |
| | Polyvinylpyrrolidone (molecular weight: $1.6 \times 10^5$) | 16.2 mg |
| | Low substituted hydroxypropylcellulose | 87.6 mg |
| | Carnauba wax | 54.1 mg |
| | Paraffin wax | 54.1 mg |
| | Magnesium stearate | 0.5 mg |
| | | 270.9 mg |
| (3) | Chloropyridine compound | 58.4 mg |
| | Polyvinylpyrrolidone (molecular weight: $4.0 \times 10^4$) | 16.2 mg |
| | Low substituted hydroxypropylcellulose | 87.6 mg |
| | Carnauba wax | 54.1 mg |
| | Paraffin wax | 54.1 mg |
| | Magnesium stearate | 0.5 mg |
| | | 270.9 mg |
| (4) | Chloropyridine compound | 58.4 mg |
| | Polyvinylpyrrolidone (molecular weight: $1.0 \times 10^4$) | 16.2 mg |
| | Low substituted hydroxypropylcellulose | 87.6 mg |
| | Carnauba wax | 54.1 mg |
| | Paraffin wax | 54.1 mg |

| | -continued | |
|---|---|---|
| | Magnesium stearate | 0.5 mg |
| | | 270.9 mg |

EXAMPLE 11

Dihydropyridine A compound is converted into a solid dispersion composition containing dihydropyridine A compound and hydroxypropylmethylcellulose (c.v 6 cps) according to a similar manner to that of Example 1 and then according to a similar manner to that of Example 7, tablets each having the composition given below are prepared.

| (1) | Dihydropyridine A compound | 8.0 mg |
|---|---|---|
| | Hydroxypropylmethylcellulose (c.v. 6 cps) | 24.0 mg |
| | Low substituted hydroxypropylcellulose | 36.0 mg |
| | Lactose | 12.0 mg |
| | Pullulan (molecular weight: $3.0 \times 10^5$) | 8.9 mg |
| | Hydrogenated soybean oil | 88.9 mg |
| | Magnesium stearate | 0.4 mg |
| | | 178.2 mg |
| (2) | Dihydropyridine A compound | 8.0 mg |
| | Hydroxypropylmethylcellulose (c.v. 6 cps) | 24.0 mg |
| | Low substituted hydroxypropylcellulose | 36.0 mg |
| | Lactose | 12.0 mg |
| | Pullulan (molecular weight: $2.0 \times 10^5$) | 8.9 mg |
| | Hydrogenated soybean oil | 88.9 mg |
| | Magnesium stearate | 0.4 mg |
| | | 178.2 mg |
| (3) | Dihydropyridine A compound | 8.0 mg |
| | Hydroxypropylmethylcellulose (c.v. 6 cps) | 24.0 mg |
| | Low substituted hydroxypropylcellulose | 36.0 mg |
| | Lactose | 12.0 mg |
| | Pullulan (molecular weight: $1.0 \times 10^5$) | 8.9 mg |
| | Hydrogenated soybean oil | 88.9 mg |
| | Magnesium stearate | 0.4 mg |
| | | 178.2 mg |

Regarding the tablets prepared according to the present invention, the penetration of water is limited to the surface layer of the tablet and with the progress of said penetration of water the disintegrating agent in the inner granules (i.e. the wax-treated granules in the tablet making step) within the surface layer of the tablet swells gradually and finally breaks through the surrounding wall of wax and thereby the inner granules separate from the surface layer of the tablet, so that the drug gets released therefrom (because the inner granules are made easily disintegrable).

Said process is repeated continuously and at an almost constant rate, and so the drug gets released from the tablet sustainedly and at an almost constant rate.

Namely, the rate-determining step of the drug release from the tablet of the present invention is the step where the inner granules in the surface layer of the tablet disintegrate (or separate) from the tablet, and this characteristic gives rise to the feature of the tablet of the present invention that the dissolution pattern is linear and that the dissolution pattern and the dissolution rate hardly get influenced by the change of the intensity of stirring, the pH of the aqueous medium or the like.

Ordinarily, the technique to have a tablet disintegrate is used in order to have the drug released fast from a tablet, and so in comparison with this, a distinct feature exists in the present invention.

In this respect, one can call the sustained release tablet of the present invention "slowly disintegrating tablet".

In the present invention, the disintegration of the inner granules from the tablet, in other words, the separation of the inner granules from the tablet can be controlled quite enough by adjusting the kind and/or the amount of the disintegrating agent and/or the wax and furthermore, in case that the inner granules contain the water soluble polymer, said control can be performed more precisely by further adjusting the molecular weight of the water soluble polymer to be used.

As mentioned above, since the rate-determining step is the disintegration step of the inner granules from the tablet, the control of the dissolution of the drug can be also performed by adjusting above-mentioned factors.

In the following, in order to illustrate the effect obtained by the present invention, the representative test results are given.

Test tablets

Test tablet A :
The tablet disclosed hereinbefore in Example 1 (containing 8.0 mg of dihydropyridine A compound per tablet)

Test tablet B :
The tablet disclosed hereinbefore in Example 2 (containing 8.0 mg of dihydropyridine A compound per tablet)

Test tablet C. :
The tablet disclosed hereinbefore in Example 4 (containing 125 mg of cephalosporin A compound per tablet)

Test tablet D :
The tablet disclosed hereinbefore in Example 5 (containing 84.3 mg of cephalosporin A compound per tablet)

Dissolution and disintegration tests

Test methods
(1) The disintegration test disclosed in the Pharmacopoeia of Japan (10th eddition) (1st fluid, 15 cpm, 900 ml)
(2) The dissolution test disclosed in the Pharmacopoeia of Japan (10th eddition) (Paddle method) (1st fluid, 200 rpm, 900 ml)
(3) The dissolution test disclosed in the Pharmacopoeia of Japan (10th eddition) (Paddle method) (1st fluid, 100 rpm, 900 ml)
(4) The dissolution test disclosed in the Pharmacopoeia of Japan (10th eddition) (Paddle method) (2nd fluid, 100 rpm, 900 ml)
(5) The modified disintegration test (1st fluid, 15 cpm, 10 ml)
(6) Sartorius method (1st fluid, 100 ml)
(7) Sartorius method (2nd fluid, 100 ml) (The test solution used in dissolution tests were the same as those used in disintegration tests. All the tests were performed at 37° C.)

[I] To investigate the influence of the differences of the dissolution conditions (intensity of stirring, pH of test solution) on the dissolution pattern, the dissolution percentage was determined with the passage of time under several different conditions.

TABLE 1

| Test tablet | Test method | Dissolution (%) at each time Time (hr) | | | | | | |
|---|---|---|---|---|---|---|---|---|
| | | 0.5 | 1.0 | 2.0 | 3.0 | 4.0 | 5.0 | 6.0 |
| A | (1) | 6.4 | 14.3 | 37.5 | 55.3 | 70.1 | 76.5 | 86.1 |
| | (2) | 6.7 | 15.6 | 38.7 | 55.0 | 70.1 | 76.4 | 83.2 |

TABLE 1-continued

| Test tablet | Test method | Dissolution (%) at each time Time (hr) | | | | | | |
|---|---|---|---|---|---|---|---|---|
| | | 0.5 | 1.0 | 2.0 | 3.0 | 4.0 | 5.0 | 6.0 |
| | (3) | 4.3 | 12.1 | 31.6 | 50.1 | 64.7 | — | 79.0 |
| | (4) | 5.4 | 13.8 | 33.5 | 50.8 | 63.1 | — | 77.0 |
| B | (1) | 4.2 | 6.3 | 11.2 | 18.6 | 25.1 | 34.1 | — |
| | (2) | 4.4 | 8.0 | 13.8 | 18.4 | 31.5 | 44.1 | — |
| | (3) | 4.1 | 5.7 | 10.3 | 15.6 | 23.4 | — | 38.2 |
| | (4) | 2.3 | 5.5 | 11.2 | 16.6 | 21.8 | — | 35.4 |

TABLE 2

| Test tablet | Test method | Dissolution (%) at each time Time (hr) | | | | | | |
|---|---|---|---|---|---|---|---|---|
| | | 0.5 | 1.0 | 2.0 | 3.0 | 4.0 | 5.0 | 6.0 |
| C | (2) | 2.0 | 4.1 | 20.5 | 44.2 | 66.3 | 85.4 | 99.1 |

TABLE 3

Dissolution (%) at each time

| Test tablet | Test method | Time (hr) | | | | | |
|---|---|---|---|---|---|---|---|
| | | 0.5 | 1.0 | 2.0 | 3.0 | 4.0 | 5.0 |
| D | (6) | 6.2 | 16.5 | 39.5 | 65.0 | 93.5 | 100.0 |
| | (7) | 10.0 | 21.1 | 45.2 | 69.9 | 95.8 | 100.1 |

[II] To investigate the influence of the differences of the amount of the solution of the disintegration rate of tablets, disintegration tests were performed under two different conditions

TABLE 4

| Test tablet | Test method | Disintegration percentage* (%) at each time Time (hr) | | | | | |
|---|---|---|---|---|---|---|---|
| | | 1.0 | 2.0 | 3.0 | 4.0 | 5.0 | 6.0 |
| A | (1) | 14.3 | 35.5 | 53.3 | 68.1 | 74.5 | 86.1 |
| | (5) | 15.1 | 31.2 | — | 65.0 | — | 86.2 |

*disintegration percentage (%) = $\frac{\text{Initial tablet weight (mg)} - \text{Residual tablet weight (mg)}}{\text{Initial tablet weight (mg)}} \times 100$ Blood concentration test Test 1

Four male beagle dogs (body weight 8-12 kg) which had fasted overnight were each given 100 g of Lab. Chow (a trademark of Purina-Taiyo Pet Food Co.) 30 minutes before administration of test tablets. Then, the equivalent of 8.0 mg of dihydropyridine A compound was administered to each dog. Immediately after the administration, each dog was forcedly given 40 ml of water, and thereafter allowed to freely drink water. With the passage of time after administration of test tablet, the plasma concentration of dihydropyridine A compound was determined by ECD gas chromatography.

The aforementioned test tablets A and B were used as test tablets and a tablet having the following composition was used for the control.

| (Composition of the control tablet; amounts per tablet) | |
|---|---|
| Dihydropyridine A compound | 8.0 mg |
| Hydroxypropylmethylcellulose (c.v. 6 cps) | 24.0 mg |
| Low substituted hydroxypropylcellulose | 24.0 mg |
| Lactose | 24.0 mg |
| Magnesium stearate | 0.2 mg |
| | 80.2 mg |

This control tablet was a tablet of easily soluble solid dispersion composition.

Test Results

The plasma concentration (ng/ml) at each time, in terms of mean value ± Standard Error (for four beagle dogs), is shown below in the following table.

| Test tablet | Time (hr) | | | | | | | | |
|---|---|---|---|---|---|---|---|---|---|
| | 0.5 | 1.0 | 2.0 | 4.0 | 6.0 | 8.0 | 10.0 | 12.0 | 24.0 |
| A | 7.7 ± 3.0 | 16.7 ± 5.6 | 27.9 ± 9.3 | 27.0 ± 6.7 | 16.1 ± 2.1 | 11.7 ± 4.5 | 7.9 ± 2.8 | 6.6 ± 1.7 | 0.6 ± 0.6 |
| B | 3.2 ± 1.4 | 11.6 ± 3.5 | 18.4 ± 7.6 | 14.1 ± 4.9 | 15.6 ± 1.6 | 22.5 ± 6.4 | 24.1 ± 6.8 | 10.8 ± 1.0 | 3.7 ± 1.9 |
| Control | 57.8 ± 16.1 | 65.5 ± 3.6 | 44.3 ± 7.2 | 20.4 ± 2.4 | 11.0 ± 1.4 | 7.1 ± 0.6 | 5.0 ± 0.3 | 3.6 ± 0.3 | 0.0 ± 0.0 |

Test 2

Six male beagle dogs (body weight 8-12 kg) which had fasted overnight were each given 100 g of Lab. Chow (a trademark of Purina-Taiyo Pet Food Co.) 30 minutes before administration of test tablets. Then, the equivalent of 250 mg of cephalosporin A compound per dog was administered. Immediately after the administration, each dog was forcedly given 40 ml of water and, thereafter, allowed to freely drink water. With the passage of time after administration of the test tablet, the serum concentration of cephalosporin A compound was determined by liquid chromatography.

The test tablet was the aforementioned test tablet C. and an aqueous solution of cephalosporin A compound was used as the control.

(Preparation of the control aqueous solution)

Cephalosporin A compound was dissolved in phosphate buffer (pH 6.0) to give a 1.25 (weight/volume) % aqueous solution. In the test, 20 ml of this aqueous solution (250 mg as cephalosporin A compound) was administered.

Test results

The serum concentration (μg/ml) at each time, in terms of mean value ± Standard Error (for six beagle dogs), are shown below in the following table.

| Test tablet | Time (hr) | | | | | | | |
|---|---|---|---|---|---|---|---|---|
| | 0.5 | 1.0 | 2.0 | 4.0 | 6.0 | 8.0 | 11.0 | 24.0 |
| C | 0.19 ± 0.19 | 0.00 ± 0.00 | 1.47 ± 0.54 | 5.01 ± 1.36 | 10.90 ± 2.58 | 12.62 ± 2.81 | 11.26 ± 3.32 | 4.27 ± 1.08 |
| Control | 5.53 ± 0.56 | 10.00 ± 1.66 | 11.95 ± 2.33 | 10.58 ± 1.79 | 9.35 ± 1.53 | 7.62 ± 1.31 | 4.88 ± 0.98 | 1.93 ± 0.29 |

Comparing the results on the test methods (1) to (3) in the dissolution test results given in Table 1, it turned out that, in each case, the dissolution pattern was nearly linear and there was not much difference among each dissolution rate. And the dissolution test results given in Table 2 also revealed that the dissolution patterns were nearly linear.

From above results, it turned out that the tablets of the present invention had the characteristic that even if the method of stirring or the intensity of stirring changed, the dissolution pattern was almost linear (namely, the dissolution rate was nearly constant) and further the dissolution rate was hardly influenced by the changes of the dissolution conditions.

Further, comparing the results on the test methods (3) and (4), given in Table 1 and comparing the results on the test methods (6) and (7), given in Table 3, it turned out that, in each case, each dissolution pattern on two test methods was linear and each dissolution rate on two test methods was almost the same.

From these results, it became clear that both the dissolution pattern and the dissolution rate were hardly influenced by the change of the pH value of the dissolution medium.

Furthermore, in spite of the fact that the solubility of cephalosporin A compound changes on account of the change of the pH of the dissolution medium because cephalosporin A compound has carboxy group and amino group in the molecule, when the present invention was applied to said compound, it turned out that the dissolution patterns in the different pH mediums were almost the same (Please make reference to the results given in Table 3) (The pH of the 1st fluid is about 1.2 and the pH of the 2nd fluid is about 6.8. The solubility of cephalosporin A compound is 1.9 mg/ml in the 1st fluid and more than 400 mg/ml in the 2nd fluid).

Accordingly, it is quite useful to apply the present invention to a drug whose solubility changes depending on the pH of the aqueous medium.

From the disintegration test results given in Table 4, it turned out that not only in case that there was a lot of solution, but also in case that there was only a little solution, the disintegration percentage changed linealy with the passage of time and the disintegration rate on each test method was similar to each other.

Since regarding the tablet of the present invention, the disintegration step is the rate-determining step, the same is true of dissolution.

Since in the digestive tract, the amount of water is liable to vary depending on the site of the digestive tract or time course, the tablet of the present invention is adaptable to the variation of the circumstance as stated above, and so very practical.

Furthermore, the results of the blood concentration tests revealed that the maintenance of blood concentration of the drug could be obtained, as expected from the results of the dissolution tests and the disintegration tests. And it was also shown that by changing the composition of the components (i.e. the kind and/or the amount of the disintegrating agent and/or the wax as mentioned before), the time taken to reach the maximum blood concentration or the like, could be controlled.

As shown above, the tablets of the present invention have excellent effects and the dissolution rate and the duration of the dissolution therefrom can be simply controlled by adjusting the kind and/or the amount of the disintegrating agent and/or the wax and so have overcome the drawbacks that various pharmaceutical preparations of the prior art have.

Incidentally, as mentioned before, sustained release tablets of the present invention may contain water soluble polymer, namely, may comprise easily disintegrable granules containing drug together with water soluble polymer, and wax.

In this case, the duration of the drug release or the like can be controlled more precisely by further adjusting the molecular weight of the water soluble polymer to be used. But please note that said control can be performed, of course, by changing the above-mentioned factors (i.e. the kind and/or the amount of the disintegrating agent and/or the wax).

In the following, in order to illustrate the effect of the adjusting the molecular weight of the water soluble polymer, the representative test results are given.

Test tablets

Test tablet E :
The tablet disclosed hereinbefore in Example 7
Test tablet F :
The tablet disclosed hereinbefore in Example 8 (1)
Test tablet G :
The tablet disclosed hereinbefore in Example 8 (2)
Test tablet H :
The tablet disclosed hereinbefore in Example 8 (3)
(Each test tablet contains 83.3 mg of cephalosporin A compound per tablet.)

Test method (Dissolution test)

Test method X : The dissolution test disclosed in the Pharmacopoeia of Japan (10th eddition) (Paddle method, 1st fluid, pH 1.2, 100 rpm, 900 ml, 37° C.)
Test method Y : The dissolution test disclosed in the Pharmacopoeia of Japan (10th eddition) (Paddle method, 2nd fluid, pH 6.8, 100 rpm, 900 ml, 37° C.)

Test results

Dissolution (%) at each time

| Test tablet | Test method | Time (hr) | | | | | | | |
|---|---|---|---|---|---|---|---|---|---|
| | | 0.5 | 1.0 | 2.0 | 3.0 | 4.0 | 5.0 | 6.0 | 7.0 |
| E | X | 2.7 | 5.6 | 11.1 | 19.4 | 27.9 | 36.2 | 44.6 | 52.4 |
| | Y | 5.1 | 9.0 | 16.6 | 22.5 | 30.1 | 38.4 | 45.8 | 53.7 |
| F | X | 2.3 | 5.0 | 12.4 | 21.2 | 32.3 | 44.6 | 55.1 | 65.6 |
| G | X | 4.0 | 9.8 | 21.8 | 33.9 | 48.8 | 60.6 | 72.5 | 82.7 |
| | Y | 7.3 | 14.5 | 27.5 | 40.6 | 55.6 | 68.2 | 78.1 | 88.0 |
| H | X | 3.8 | 9.8 | 26.5 | 44.1 | 60.3 | 75.7 | 85.3 | 91.8 |

From above results, it was shown that in each case the dissolution percentage changed almost linealy with the passage of time, namely, even if the molecular weight of the water soluble polymer changed, the feature of the tablet of the present invention that dissolution rate was almost constant was retained.

Comparing the result on test method X with that on test method Y on test tablets E and G, it turned out that there was only a little difference between the dissolution patterns and between the dissolution rate.

That is, it became clear that, even if the molecular weight of the water soluble polymer changed, the independency of the dissolution pattern and rate on the pH of the dissolution medium was retained.

And it turned out that from the above results, the higher the viscosity of the water soluble polymer (namely, the molecular weight of the water soluble polymer) became, the longer the duration of the dissolution became.

As stated above, it is possible to adjust the properties of the tablets of the present invention such as the duration of the dissolution, the dissolution rate or the like by adjusting the molecular weight of the water soluble polymer to be used without losing the features such as almost constant dissolution rate, the independency of dissolution pattern on the pH of the dissolution medium or the like.

Therefore, it is possible to adjust the properties of the tablets more precisely by the combination of adjusting the kind and/or the amount of the disintegrating agent, adjusting the kind and/or the amount of the wax and adjusting the molecular weight of the water soluble polymer.

As discussed in the above specification, sustained release tablets each comprising easily disintegrable granules, each containing drug, and wax; and sustained release tablets each comprising easily disintegrable granules, each containing drug together with water soluble polymer, and wax according to the present invention, both have various quite excellent effects and have overcome various problems of the prior art, and so are quite useful.

What we claim is:

1. A sustained release tablet which comprises easily disintegrable granules containing
    (a) a drug,
    (b) a disintegrating agent selected from the group consisting of starch derivatives, gums, cellulose derivatives and ion-exchange resins, and
    (c) a water soluble polymer selected from the group consisting of cellulose derivatives, synthetic water soluble polymers and polysaccharides, the surfaces of which granules are treated solely with a wax selected from the group consisting of plant or animal wax, hydrogenated oils and paraffin.

2. A sustained release tablet which comprises easily disintegrable granules containing
    (a) a drug,
    (b) a disintegrating agent selected from the group consisting of starch derivatives, gums, cellulose derivatives and ion-exchange resins,
    (c) a water soluble polymer selected from the group consisting of cellulose derivatives, synthetic water soluble polymers and polysaccharides, and
    (d) an excipient selected from the group consisting of lactose, sucrose and mannitol, the surfaces of which granules are treated solely with a wax selected from the group consisting of plant or animal wax, hydrogenated oils and paraffin.

3. A sustained release tablet of claim 1 or 2, wherein the drug is selected from the group consisting of dihydropyridine A compound, cephalosporin A compound and chloropyridine compound.

4. A sustained release tablet of claim 3, wherein the disintegrating agent is a cellulose derivative.

5. A sustained release tablet of claim 4, wherein the amount of the disintegrating agent is 10 to 60 weight percent of the whole granule components, the amount of water soluble polymer is 2 to 45 weight percent of the whole granule components, and the amount of wax is 20 to 65 weight percent of the whole components of the tablet.

6. A sustained release tablet of claim 5, which comprises easily disintegrable granules consisting of
    (a) dihydropyridine A compound as a drug,
    (b) low-substituted hydroxypropylcellulose as a disintegrating agent,
    (c) hydroxypropylmethylcellulose or pullulan as a water soluble polymer, and
    (d) lactose as an excipient, the surfaces of which granules are treated solely with a wax selected from the group consisting of carnauba wax, hydrogenated soybean oil and paraffin wax, wherein the amount of disintegrating agent is about 24 to about 45 weight percent of the whole granule components, the amount of water soluble polymer is about 30 to about 38 weight percent of the whole granule components, and the amount of wax is about 40 to about 50 weight percent of the whole components of the tablet.

7. A sustained release tablet of claim 6, wherein the water soluble polymer is hydropropylmethylcellulose, and the wax is hydrogenated soybean oil.

8. A sustained release tablet of claim 7, wherein the amount of low substituted hydroxypropylcellulose is about 45 weight percent of the whole granule components, the amount of hydroxypropylmethylcellulose is about 30 weight percent of the whole granule components, and the amount of hydrogenated soybean oil is about 50 weight percent of the whole components of the tablet.

9. A sustained release tablet of claim 6, wherein the water soluble polymer is hydroxypropylmethylcellulose, and the wax is a combination of carnauba wax and paraffin wax.

10. A sustained release tablet of claim 6, wherein the water soluble polymer is a combination of hydroxypropylmethylcellulose and pullulan, and the wax is hydrogenated soybean oil.

11. A sustained release tablet of claim 5, which comprises easily disintegrable granules consisting of
    (a) cephalosporin A compound as a drug,
    (b) low substituted hydroxypropylcellulose as a disintegrating agent, and
    (c) hydroxypropylmethylcellulose as a water soluble polymer, the surfaces of which granules are treated solely with a wax selected from the group consisting of carnauba wax, hydrogenated soybean oil and hydrogenated castor oil, wherein the amount of disintegrating agent is about 24 to about 40 weight percent of the whole granule components, the amount of water soluble polymer is about 2 to about 10 weight percent of the whole granule components, and the amount of wax is about 40 to about 50 weight percent of the whole components of the tablet.

12. A sustained release tablet of claim 5, which comprises easily disintegrable granules consisting of
    (a) chloropyridine compound as a drug,
    (b) low substituted hydroxypropylcellulose as a disintegrating agent,
    (c) hydroxypropylmethylcellulose or polyvinylpyrrolidone as a water soluble polymer, the surfaces of which granules are treated solely with a wax selected from the group consisting of carnauba wax, hydrogenated soybean oil, hydrogenated castor oil and paraffin wax,
    wherein the amount of disintegrating agent is about 54 weight percent of the whole granule components, the amount of water soluble polymer is about 10 weight percent of the whole granule components, and the amount of wax is about 40 to about 50 weight percent of the whole components of the tablet.

13. A method of preparing a sustained release tablet, which comprises
(a) preparing easily disintegrable granules containing
(1) a drug,
(2) a disintegrating agent selected from the group consisting of starch derivatives, gums, cellulose derivatives and ion-exchange resins, and
(3) a water scluble polymer selected from the group consisting of cellulose derivatives, synthetic water soluble polymers and polysaccharides,
(b) treating said granules solely with a wax selected from the group consisting of plant or animal wax, hydrogenated oils and paraffin, and
(c) compressing the resultant wax-treated granules into tablets.

* * * * *